United States Patent
Miljkovic et al.

(10) Patent No.: US 6,924,269 B2
(45) Date of Patent: Aug. 2, 2005

(54) ENZYME INHIBITORS AND METHODS THEREFOR

(75) Inventors: Dusan Miljkovic, San Diego, CA (US); Pietrzkowski Zbigniew, San Diego, CA (US)

(73) Assignee: VDF Futureceuticals, Inc., Momence, IL (US)

( * ) Notice: Subject to any disclaimer, the term of this patent is extended or adjusted under 35 U.S.C. 154(b) by 0 days.

(21) Appl. No.: 10/310,380

(22) Filed: Dec. 4, 2002

(65) Prior Publication Data

US 2004/0110724 A1 Jun. 10, 2004

(51) Int. Cl.[7] .................. A61K 31/70; A61K 31/69; C07F 5/02
(52) U.S. Cl. .................. 514/23; 514/64; 568/1
(58) Field of Search .................. 514/23, 64; 568/1

(56) References Cited

U.S. PATENT DOCUMENTS 5,312,816 A * 5/1994 Spielvogel et al. ........... 514/64
6,080,425 A * 6/2000 Miljkovic et al. ........... 424/450

OTHER PUBLICATIONS

Sui et al. (Bioorganic & Medicinal Chemistry, Dec. 1993, vol. 1 (6), pp. 415–422) (Abstract Sent).*

Murmu et al. (Journal of Experimental & Clinical Cancer Research (2001), 20 (4), 511–515) (Abstract Sent).*

* cited by examiner

*Primary Examiner*—James O. Wilson
*Assistant Examiner*—Michael C. Henry
(74) *Attorney, Agent, or Firm*—Rutan & Tucker, LLP

(57) ABSTRACT

An enzyme is inhibited by presenting the enzyme with a boron containing structure having a tetrahedral boron atom covalently bound to four ligands. Particularly preferred enzymes include prostaglandin endoperoxide synthase (COX-1 and COX-2), and particularly preferred structures include a ligand that confers at least 80-fold selectivity of COX-2 inhibition over COX-1 inhibition. Consequently, further methods are directed towards induction of apoptosis in a cell and methods of reducing pain.

23 Claims, 2 Drawing Sheets

Type 1       Type 2      Type 3

4 Monodentate Ligands     2 Monodentate Ligands,     2 Bidentate Ligands

1 Bidentate Ligand

Type 4      Type 5

1 Tridentate Ligand,     1 Tetradentate Ligands

1 Monodentate Ligand

X, Y, Z, and W are independently Hetero-atoms as defined above

ENZYME INHIBITORS AND METHODS THEREFOR

FIELD OF THE INVENTION

The field of the invention is enzyme inhibitors.

BACKGROUND OF THE INVENTION

Enzymes not only play a crucial role in synthesis, degradation and maintenance of numerous metabolites, but are also intimately involved in generation and degradation of biological messenger molecules that affect various pathways. One particularly significant enzyme involved in the inflammatory signaling pathway is the cyclooxygenase COX-2, also known as prostaglandin endoperoxide synthase (EC 1.14.99.1).

COX-2 is a bifunctional inducible enzyme (homodimer with a heme as cofactor) catalyzing the first committed step in the synthesis of prostaglandins, thomboxanes and other eicosanoids. There are two overall reactions catalyzed by cyclooxygenase. The first reaction is a cyclooxygenase reaction that requires two molecules of molecular oxygen. The end product of this reaction is the formation of Prostaglandin-G2. The second reaction is a peroxidase reaction that generates the final product Prostaglandin-H2.

It was hypothesized by Flower and Vane in 1972 (Nature, 240; 410–411) that more than one isozyme of cyclooxygenase may exist. Definitive proof for the existence of two isozymes (COX-1 and COX-2) of cyclooxygenase was finally shown in 1991 by Xie et al. (PNAS, 88, 2692–2692).

COX-1 is found throughout the body and it is considered constitutively expressed. It is found in abundance in the gastrointestinal track, where it produces prostaglandins (prostacyclin, PGI2, PGE2 etc.) that are considered cytoprotective. COX-1 is also found in abundance in the kidneys and in platelets.

COX-2 expression is inducible by inflammatory cytokines such as: Interleukins-1b i.e (IL)-1, and (IL)-2, Tumor Necrosis Factor-a (TNF)-a, growth Factors, and COX-2 expression is repressed by anti-inflammatory cytokines such as IL-4, IL-10, IL-13, and Glucocorticoids. COX-2 derived prostaglandins are considered deleterious because they are found mainly at the sites of inflammation and are thought to trigger, participate in, or exacerbate the inflammation process.

COX-2 Inhibitors

It is generally believed that COX-2 specific inhibitors will reduce pain, fever, and inflammation without causing gastrointestinal or renal injury. There are two central tenets to this hypothesis: First, the prostaglandins that mediate inflammation, fever and pain are produced solely via COX-2. Second, prostaglandins that are important in gastrointestinal and renal function are produced solely via COX-1. Thus, it is thought that the toxicity of non-steroidal anti-inflammatory drugs (NSAIDS) in the GI and renal systems may be due to a lack of selectivity of those drugs with respect to inhibition of COX-1 and COX-2. Consequently, numerous scientists attempted to provide COX-2 selective inhibitors that would lead to a powerful drug without the adverse side-effects of COX-2 inhibitors that also affect COX-1, and various naturally occurring compounds and synthetic compounds were discovered with at least some degree of COX-2 specificity.

For example, curcumin, a naturally occurring compound has been reported to exhibit anti-inflammatory and analgesic activity (Satoskar R, et al. Evaluation of anti-inflammatory property of curcumin (diferuloyl methane) in patients with postoperative inflammation. Int. J. Clin. Pharmacol. Ther. Toxicol. 1986;24(12):651–4.). Moreover, recent in vitro studies suggest inhibition of the expression and activity of COX-2 in several different gastrointestinal cell lines, including colon, esophagus and small intestine (Zhang F, et al. Curcumin inhibits cyclooxygenase-2 transcription in bile acid- and phorbol ester-treated human gastrointestinal epithelial cells. Carcinogenesis 1999;20(3):445–51).

In another example, Thunder God vine extracts exhibited significant inhibition of COX-2 translation without any appreciable effect on COX-2 transcription or COX-2 activity. Moreover, COX-1 protein expression was unaltered by the plant extract (Lipsky P E, Tao X L. A potential new treatment for rheumatoid arthritis: thunder god vine. Semin Arthritis Rheum 1997;26(5):713–23). In a still further example, resveratrol was demonstrated to reverse a phorbol ester induced increase in COX-2 mRNA and protein in human mammary and oral epithelial cells. In addition to modifying gene expression, it was also found that resveratrol directly inhibits COX-2 activity (Subbaramaiah K, et al. Resveratrol inhibits cyclooxygenase-2 transcription and activity in phorbol ester-treated human mammary epithelial cells. J Biol Chem 1998;273(34):21875–82).

Synthetic COX-2 inhibitors include selected salicylic acid compounds (e.g., acetyl salicylic acid, sodium salicylate, salsalate, diflunisal, salicylsalicylic acid, sulfasalazine, or olsalazine) and various para-aminophenol derivatives (e.g. acetaminophen). While such inhibitors generally are relatively strong COX-2 inhibitors, selectivity over COX-1 is frequently not as high as one would desire. Similarly, other COX-2 inhibitors including several indole and indende acetic acids (e.g. indomethacin, sulindac, etodolac), various heteroaryl acetic acids (e.g. Tolmetin, diclofenac, ketorolac), selected arylpropionic acids (e.g. ibuprofen, naproxen, flubiprofen, ketoprofen, fenoprofen, oxaprozin), and selected anthranilic acids (e.g. mefenamic acid, meclofenamic acid) will exhibit at least some undesirably high COX-1 inhibition. Further known relatively unspecific COX-2 inhibitors include various enolic acids (e.g. piroxican, tenoxicam), various pyrazolidinediones (e.g., phenylbutazone, oxyphenthratrazone), and selected alkanones (e.g. Nabumetone).

Although many of the above listed drugs are effective to at least some degree, the anti-inflammatory, analgesic, antifever and anti-thrombotic effect is frequently associated with in some cases substantial COX-1 inhibition. Unfortunately, COX-1 inhibition is thought to suppress various important functions, including repair and maintenance of stomach lining, which results in varying degrees of gastric ulcerations, perforations or obstructions in one-third to almost one-half of patients taking such drugs (Fries J. Toward an understanding of NSAID-related adverse events: the contribution of longitudinal data. Scand J Rheumatol Suppl 1996;102:3–8). Moreover, on the extreme end, more than 16,500 people die in the United States each year from NSAID-related gastrointestinal bleeding (Singh G. Recent considerations in nonsteroidal anti-inflammatory drug gastropathy. Am J Med 1998;105(1B)).

Recent developments finally resulted in various compounds with relatively high COX-2 specificity, and among those are Celecoxib (Celebrex; 4-(5-(4-Methylphenyl)-3-(trifluoromethyl)-1H-pyrazol-1-yl)benzenesulfonamide) and rofecoxib (Vioxx; 3-phenyl-4-(4-(methylsulfonyl)phenyl))-2(5H)-furanone). However, while these compounds exhibit desirable IC50 values at relatively good COX-2 specificity, such compounds are typically expensive and not well tolerated in some patients, especially overt a prolonged period of administration.

Boron-containing Compounds as Enzyme Inhibitors

Boron compounds are known to show a variety of different biological activities. Very often, boron compounds show enzyme inhibitory activity, and various boron compounds have been shown to inhibit a number of enzymes alone or in a mixture with various co-inhibitors. For example, borates inhibit L-amino acid oxidase in a mixture with butanedione by interacting with the arginine residue in the active site. (Christman M F, Cardenas J M: Experientia 38 (5): 537–538 (1982)).

Similarly, borates and butanedione inhibit citrate/isocitrate-hydro-lyase, EC 4.2.1.3, again by interacting with the arginine residue from the active site. (Gawron O, Jones L: Biochem Biophys Acta 484 (2): 453–464 (1977)). Also, 2,3-butanedione or 1,2-cyclohexanedione in the presence of borates interact specifically with the guanidino group from arginine, and this fact was used for determination of arginine residues in the active site of the examined enzymes. In this way Dietl, T. and Tschesche, H. (Hoppe Seylers Z Physiol Chem: 357 (5): 657–665 (1976)) proved arginine residue is present in the active site of proteinases.

Borates (at low concentration) are also known to inhibit glyceraldehyde-3-phosphate dehydrogenase from human, pig and rabbit muscle. However, in greater concentration (above 6mM) borates inhibit esterase and acetylphosphatase activities. (Wolny M: Eur J Biochem 80 (2): 551–556 (1977)). Borates are also thought to inhibit methylation of catechol estrogen and pyrocatechol by catechol-O-methyltransferase (Beattie J H, Weersink E: J Inorg Biochem 46 (3): 153–160 (1992)).

Thus, although numerous compositions and methods for enzyme inhibition, and especially COX-2 inhibition are known in the art, all or almost all of them suffer from various disadvantages. Therefore, there is still a need to provide improved methods and compositions for enzyme inhibition, and especially for selective COX-2 inhibition.

SUMMARY OF THE INVENTION

The present invention is generally directed to compositions and uses of Boron containing compounds/complexes as biologically active molecules.

In one aspect of the inventive subject matter, a method of inhibiting an enzyme includes a step in which the enzyme is presented with a boron containing structure having a tetrahedral boron atom covalently bound to four ligands at a concentration effective to inhibit the enzyme, wherein particularly preferred enzymes include a prostaglandin endoperoxide synthase (e.g., COX-1 and/or COX-2).

Contemplated ligands will typically include an atom selected from the group consisting of oxygen, nitrogen, carbon, and sulfur, wherein the boron is covalently bound to the atom, and in a further contemplated aspect the boron atom is bound to the ligand to form a five- or six-membered ring comprising the boron atom, two hetero-atoms and two or three carbon atoms. Consequently, suitable ligands include a saccharide, an amino acid, a salicylic acid, and/or an ascorbic acid.

In still further contemplated aspects, the boron containing structure may include a cation, and an exemplary structure comprises potassium boroascorbate. Moreover, it is contemplated that suitable boron containing structures form a complex having an association constant of at least 50, and more typically between 3,000 to about 20,000.

In a further aspect of the inventive subject matter, a method of inducing apoptosis in a cell includes a step in which the cell is presented with a boron containing structure having a tetrahedral boron atom covalently bound to four ligands at a concentration effective to induce apoptosis. Contemplated cells particularly include neoplastic cells, and especially colon cancer cells.

In yet another aspect of the inventive subject matter, a method of reducing pain in a patient includes a step in which a boron containing structure having a tetrahedral boron atom covalently bound to four ligands is administered to a patient at a dosage effective to reduce pain. Contemplated pains include those that are not associated with an inflammatory condition (e.g., head ache, tooth ache, and/or a premenstrual pain).

Various objects, features, aspects and advantages of the present invention will become more apparent from the following detailed description of preferred embodiments of the invention, along with the accompanying drawing.

DETAILED DESCRIPTION

Figure 1:
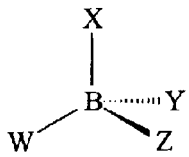
FIG. 1 is a schematic depicting exemplary types of contemplated boron containing structures.
Figure 1:
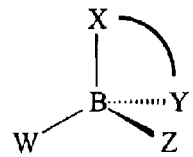
Figure 1:
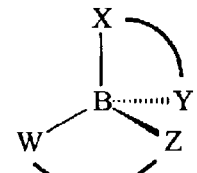
Figure 1:
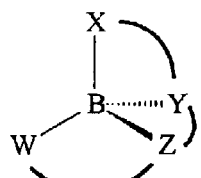
Figure 1:
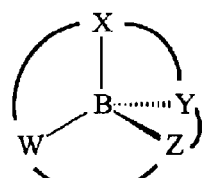

The inventors surprisingly discovered that a boron containing structure with a tetrahedral boron atom covalently bound to four ligands exhibits inhibitory action on various enzymes, and particularly on prostaglandin endoperoxide synthases COX-1 and COX-2. Moreover, the inventors discovered that the specificity towards a particular enzyme (e.g., a cyclooxygenase or other enzyme) is at least in part determined by the particular choice of ligand(s) in the boron containing structure. Consequently, it is contemplated that a broad variety of boron containing structures may be employed towards inhibition of various enzymes, and that such numerous boron containing structures may therefore be particularly useful in various methods of use, including specific inhibition of COX-2, reduction of pain in a patient, and induction of apoptosis.

Contemplated Compounds

It is generally contemplated that suitable boron containing structures include a tetrahedral boron atom that is covalently bound to four ligands. The term "tetrahedral boron atom" as used herein refers to a boron atom to which four ligands are covalently bound such that the boron atom is located at or near the center of an imaginary trigonal pyramid and in which the four ligands are located at or near the four comers of the pyramid, respectively. Viewed from another perspective, the angle between a first ligand and the boron atom and a second ligand and the boron atom will typically be about 120+/−30, wherein the deviation from the 120 degree angle will predominantly be determined by the configuration (steric hindrance, or covalent bond between at least two ligands) of the ligands.

With respect to the ligands, it is generally contemplated that the ligands may be identical or different, and that the ligands will typically comprise hetero-atoms. As used herein, the term "hetero-atom" refers to any chemical element except boron. However, in preferred aspects of the inventive subject matter hetero-atoms include oxygen, nitrogen, carbon and sulfur, while less preferred hetero-atoms include hydrogen, and non-metallic elements from groups IVA, VA, VIA and VIIA of the periodic table. In further preferred aspects, the ligands are typically covalently bound to other atoms and thereby form a molecules. Especially preferred molecules include small molecules (i.e., with a molecular weight of less than 500), and may therefore include substituted and unsubstituted alkyls, substituted and unsubstituted alkenyls, substituted and unsubstituted alkaryls, substituted and unsubstituted aryls, all of which may further comprise one or more non-carbon atom.

The terms "alkyl" and "unsubstituted alkyl" are used interchangeably herein and refer to any linear, branched, or cyclic hydrocarbon in which all carbon-carbon bonds are single bonds. Similarly, the terms "alkenyl" and "unsubstituted alkenyl" are used interchangeably herein and refer to any linear, branched, or cyclic alkyl with at least one carbon-carbon double bond. Furthermore, the terms "alkynyl" and "unsubstituted alkynyl" are used interchangeably herein and refer to any linear, branched, or cyclic alkyl or alkenyl with at least one carbon-carbon triple bond. The terms "aryl" and "unsubstituted aryl" are used interchangeably herein and refer to any aromatic cyclic alkenyl or alkynyl. The term "alkaryl" is employed where the aryl is further covalently bound to an alkyl, alkenyl, or alkynyl.

The term "substituted" as used herein refers to a replacement of a chemical group or substituent (typically H or OH) with a functional group, and particularly contemplated functional groups include nucleophilic (e.g., —$NH_2$, —OH, —SH, —NC, etc.) and electrophilic groups (e.g., C(O)OR, C(X)OH, etc.), polar groups (e.g., —OH), non-polar groups (e.g., aryl, alkyl, alkenyl, alkynyl, etc.), ionic groups (e.g., —$NH_3^+$), and halogens (e.g., —F, —Cl), and all chemically reasonable combinations thereof.

For example, suitable small molecules that include one or more ligands may therefore include various carbohydrates (e.g., fructose, glucose, mannose, arabinose, lactose), amino acids (e.g., serine, threonine, and numerous other natural and non-natural amino acids in D- and L-configuration), polyalcohols (e.g., xylitol), polyethers (e.g., polyglycols), substituted carbocyclic compounds (e.g., ascorbate, salicylate), carboxylic acids (e.g., glycolic acid, malic acid), etc. Consequently, contemplated boron containing structures can be natural, synthetic, or some combination of natural and synthetic. Thus, it is contemplated to use boron complexes which exist in nature such as glyco-borates and sugar polyols complexed with borates, both of which are often found in fruits. For practical reasons, these naturally occurring boron compounds are best synthesized, although theoretically they could be extracted from natural sources.

Boron containing structures according to the present invention can be prepared in any suitable manner. In an exemplary synthesis, sodium borate/tetraborate is treated with two molar equivalents of sugar polyol (preferably mannitol or xylytol), or two molar equivalents of an amino acid (preferably serine or threonine), in an aqueous solution. Where the aqueous solution is employed for further use, it should be recognized that isolation of the formed boron containing structure is typically not necessary. On the other hand, where desired, the isolation of the boron containing structure is readily achievable. For example, an excess of ethanol may be added to an aqueous solution of a boron containing structure, whereupon the boron containing structure will crystallize out in most cases. The so obtained solid product can the be recrystallized if needed. It is further contemplated that other ligands (mono-, di- and/or polyvalent), in the corresponding molar ratio to the starting boron compound, can be simply mixed in an appropriate solvent (e.g., water, acetone, dioxan, tetrahydrofuran, etc), whereupon the boron containing structure may directly crystallize out, or stay in a solution.

In still further contemplated aspects, the boron containing structure is positively or negatively charged, and it is contemplated that the charge of the boron containing structure is neutralized with one or more counter ion. Contemplated counter ions include ionic forms of atoms and/or molecules, and it is generally contemplated that the particular use of the boron containing structure will determine at least in part the particular nature of the counter ion. In one preferred aspect, the counter ion is a metal ion, and particularly useful counter ions include various metallic cations (e.g., sodium, potassium, calcium, or magnesium, chloride, bromide, sulfate, carbonate). However, in alternative aspects, organic charged molecules may be included and exemplary organic charged molecules are ammonium cations, protonated amines, as well as various quaternary ammonium cations. Moreover, it should also be recognized that contemplated compounds may be in complex with other contemplated compounds. For example, one bivalent metal cation may neutralize a single negative electric charge of two boron containing structures, wherein the metal cation is "sandwiched" between the two boron containing structures.

Where the boron containing structure forms a complex, it is generally preferred that such complexes exhibit a relatively high association constant. Typically, suitable association constants will be at or above about 50, although higher constants (above 1000) are generally more preferable, and most typically will be in the range between about 3,000 and about 20,000.

Figure 2A:
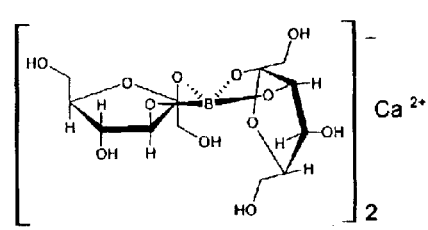
FIGS. 2A–2C are chemical structures depicting exemplary boron containing compounds.
Figure 2B:
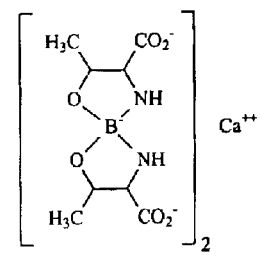
Figure 2C:
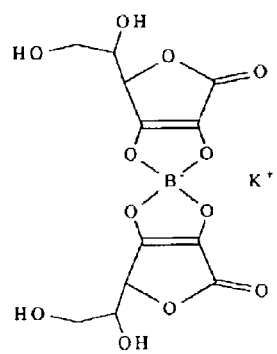

Exemplary general structures of boron compounds are depicted in FIG. 1. Ligands W, X, Y and Z may be the same as, or different from one another, and are contemplated to include any suitable hetero-atom. Where one or more of the ligands form a ring, it is contemplated that five-membered rings are preferred over six-membered rings, and that six-membered rings are preferred over seven-membered rings, and so forth. FIG. 2A depicts one particularly preferred compound, calcium fructoborate. FIG. 2B depicts another particularly preferred compound, calcium threonine borate, and FIG. 2C depicts yet another particularly preferred compound, potassium boroascorbate, wherein each of the boron containing structures are illustrated in one of several possible structural conformations.

Contemplated Enzymes and Targets affected by Contemplated Compounds

It is generally contemplated that the compounds according to the inventive subject matter will exhibit a variety of biological action on numerous targets. For example, suitable targets include enzymes, receptors, and other biomolecules involved in signal transduction or regulation of the cell cycle.

In one preferred aspect, the inventors discovered that contemplated compounds inhibit with relatively high selectivity cyclooxygenase of both isotypes (i.e., COX-1 and COX-2), wherein the selectivity was at least in part determined by the particular ligand chosen. Table 1 below depicts selective inhibition of COX-1 and COX-2 by exemplary compounds according to the inventive subject matter.

|  | Calcium Fructoborate | | Potassium Boroascorbate | |
| --- | --- | --- | --- | --- |
| Concentration | COX-1 (% Inhib.) | COX-2 (% Inhib.) | COX-1 (% Inhib.) | COX-2 (% Inhib.) |
| 100 µg/ml | 29 | 8 | −5 | 77 |
| 1000 µg/ml | 85 | 12 | −2 | 73 |
| 10 mg/ml | 95 | 10 | 69 | 71 |
| $IC_{50}$ | 222 µg/ml | >10 mg/ml | 8.57 mg/ml | <100 µg/ml |
| Selectivity | COX-1 to COX-2 at least 45-fold | | COX-2 to COX-1 at least 85-fold | |

Thus, it should be particularly appreciated that contemplated compounds not only inhibit significant inhibitory activity towards an enzyme, but also demonstrate significant specificity towards the isoenzymes of the same class of enzymes. Consequently, the inventors generally contemplate that numerous enzymes other than cylcooxygenases (prostaglandin endoperoxide synthase) may also be inhibited by contemplated compounds, and particularly contemplated enzymes include those with a heme group as cofactor in the apoenzyme. For example, contemplated enzymes with a heme group particularly include Cytochrome c peroxidases, and especially those of Mycobacterium tuberculosis (suspected in conferring resistance towards isonicotinic acid hydrazine antibiotics). Furthermore, it is generally contemplated that the enzyme may be disposed in vitro or in vivo (e.g., in a cell, organ, or organism).

Further contemplated enzymes may be classified into oxido-reductases, ligases, lyases, hydrolases, and polymerases, and it should be appreciated that a person of ordinary skill in the art may readily determine if a particular enzyme is inhibited by a particular contemplated compound. Exemplary protocols for determination of inhibition can be found, for example, in the "Handbook of Biochemical Kinetics" by Daniel L. Purich and R. Donald Allison (Academic Press; ISBN: 0125680481).

The term "inhibiting an enzyme" as used herein means that the activity of the enzyme is reduced, wherein the mode of inhibition includes competitive inhibition, non-competitive inhibition, and allosteric inhibition, but also other modes of inhibition including covalent modification, non-covalent modification, induction of conformational changes, etc.

In a further contemplated aspect of the inventive subject matter, it should be recognized that COX-2 inhibition has been linked with antineoplastic activity (see e.g., Saha et al. in World J. Surg. 2002 April 15;26(7), Dannenberg et al., in Ann N Y Acad Sci 2001 December;952:109–15, or Milas, L. in Semin Radiat Oncol. 2001 October; 11(4):290–9). Consequently, the inventors contemplate that the boron containing structures according to the inventive subject matter may target the same molecular targets than known compounds that inhibit COX-2 activity. While it is likely that such structures are COX-2, it should also be appreciated that alternative targets are also considered.

Similarly, in a further contemplated aspect of the inventive subject matter, it should be recognized that COX-2 inhibition has been linked with induction of apoptosis (see e.g., Grosch et al. in FASEB J. 2001 December; 15(14): 2742–4. or Leahy et al. in Cancer Res. 2002 February 1;62(3):625–31). Consequently, the inventors contemplate that the boron containing structures according to the inventive subject matter may target the same molecular targets than known compounds that inhibit COX-2 activity. While it is likely that such structures are COX-2, it should also be appreciated that alternative targets are also considered (see e.g., Song et al., in J. Natl. Cancer Inst. 2002 April 17;94 (8):585–91).

Contemplated Uses

In one preferred use and based on the foregoing observations, experiments and other data, the inventors contemplate that boron containing structures according to the inventive subject matter may be employed as enzyme inhibitors. Therefore, a method of inhibiting an enzyme may include a step in which the enzyme is presented with a boron containing structure having a tetrahedral boron atom that is covalently bound to four ligands at a concentration effective to inhibit the enzyme. Particularly contemplated enzymes include prostaglandin endoperoxide synthase (cyclooxygenase), and especially COX-1 and COX-2. It should further be especially appreciated that the enzyme may be in vitro or in vivo (intracellularly or extracellularly).

While numerous ligands are considered suitable for use herein (see above), it is generally preferred that at least one of the ligands (and even more preferably each of the ligands) includes an atom selected from the group consisting of oxygen, nitrogen, carbon, and sulfur, wherein the boron is covalently bound to the atom. Moreover, the boron in contemplated compounds may be bound to the ligand to form a five- or six-membered ring comprising the boron atom, two hetero-atoms and two or three carbon atoms. However, regardless of the particular structure formed, preferred ligands include various saccharides, amino acids, and/or ascorbic acid (and ascorbic acid derivatives). In further contemplated aspects, at least one of the ligands in the boron containing structure imparts an at least 80-fold selectivity of inhibition of cyclooxygenase-2 over cyclooxygenase-1, and it is especially preferred that the ligand comprises salicylic acid. Consequently, a particularly preferred compound is potassium boroascorbate. Viewed from another perspective, it is also preferred that the boron containing structure forms a complex having an association constant of at least 50, and more preferably forms a complex having an association constant between about 3,000 to about 20,000.

Furthermore, and particularly depending on the ligands in the boron containing structure, it should be recognized that the boron containing structure may have a positive or negative electrical charge. In preferred aspects, the charge may be partially or entirely neutralized by one or more ions (atomic or molecular), and an especially preferred class of ions includes a metal cation, and most preferably sodium, potassium, magnesium, or calcium.

In another preferred use, contemplated compounds may also be employed in a method of inducing apoptosis in a cell, wherein the cell is presented with a boron containing structure that has a tetrahedral boron atom covalently bound to four ligands at a concentration effective to induce apoptosis. While it is contemplated tat the nature of the cell need not be limited to a neoplastic cell, neoplastic cells and especially colon cancer cells are particularly preferred. Other contemplated cells include non-neoplastic endothelial and epithelial cells, and particularly microvascular endothelial cells. There are numerous methods known in the art to establish if apoptosis has been induced by a compound, and a collection of exemplary procedures and protocols can be found, for example, in "Apoptosis: Techniques and Protocols" by Andrea C. Leblanc (Humana Press; ISBN: 1588290123), or in "Apoptosis Detection and Assay Methods" (BioTechniques Molecular Laboratory Methods Series, 2)

by Li Zhu and Jerold Chun (Eaton Pub Co; ISBN: 1881299074).Therefore, induction of apoptosis can be identified by a person of ordinary skill in the art without undue experimentation.

In such contemplated methods of inducing apoptosis, it is generally preferred that at least one of the ligands includes an atom selected from the group consisting of oxygen, nitrogen, carbon, and sulfur, wherein the boron is covalently bound to the atom. Consequently, among other suitable ligands, preferred ligands particularly include saccharides, amino acids, and ascorbic acid (and its derivatives).

In still another preferred use, and based on the pain reduction potential of known COX-2 inhibitors (see e.g., Martinez et al. in J Pharm Pharmacol 2002 March;54(3):405–12, or Dionne et al. in Clin. Exp. Rheumatol. 2001 November–December; 19(6 Suppl 25):S63–70) the inventors contemplate that the boron containing compounds according to the inventive subject matter may be employed in a method of reducing pain in a patient. In such methods, a boron containing structure having a tetrahedral boron atom covalently bound to four ligands is administered to patient at a dosage effective to reduce pain. Particularly contemplated pain may be associated with inflammation, with an inflammatory condition (e.g., head ache, tooth ache, premenstrual pain).

Furthermore, it is contemplated that at least one of the ligands in contemplated boron containing structures used in such methods includes an atom selected from the group consisting of oxygen, nitrogen, carbon, and sulfur, wherein the boron is covalently bound to the atom. Thus, preferred ligands particularly include various saccharides, amino acids, and/or ascorbic acid (and its derivatives).

Administration (or presentation to a cell) of contemplated compounds may be many forms, including oral, parenteral (e.g., injection, transdermal, inhalation), or admixed to a cell containing medium in solid or dissolved form. Furthermore, it is contemplated that the boron containing compound(s) may be taken orally as nutritional supplements, or may be placed in solution and applied topically to the skin.

For example, where topical administration is contemplated, preferred concentrations of boron containing solutions/emulsions will have about $10^{-6}$ to 10 weight % of boron, with solutions/emulsions containing 1–5 mg of B/ml. Such solutions/emulsions are contemplated to be rubbed onto the skin twice per day, morning and evening, preferably after a shower or bath. Other contemplated protocols include applications of greater or lesser frequency, such as daily, every-other day, weekly, or bi-weekly schedules.

Consequently, some of the contemplated formulations of boron containing structures may advantageously involve a solution or emulsion of the active material in water, aqueous buffer, a mixture of water and an organic solvent allowed in topical skin treatment (such as ethanol, glycerol, etc), organic non-toxic and non-irritating solvents, or macro- and micro-emulsion forms, liposome forms, or in any other suitable carrier(s) for topical application. Particularly contemplated carriers are liposome and microemulsion formulations, and at present the most preferred carriers are emulsions of a bile acid salt (such as sodium taurocholate) and a soybean oil such as soybean phosphatidyl choline (SPC). Such formulations are contemplated to efficiently penetrate the skin stratum corneum barrier and reach the stratum spinosum, stratum basalis, and dermis. As used herein, the term "solution" is used a broad lay sense to mean any substance dispersed in a carrier. Thus, according to the definition used herein, solutions of boron containing structures will include mixtures of boron containing structures in all manner of solvents, whether homogeneously or non-homogeneously dispersed, completely or partially solvated, suspended, emulsified, or dispersed in any other manner. Further aspects of contemplated uses and formulations are described in U.S. Pat. Nos. 5985,842, 5,962,049, and 6,080,425, all to Miljkovic, and all incorporated by reference herein.

For example, where oral administration is contemplated, dosages of contemplated boron containing structures will preferably provide at least 0.1 mg of boron per individual dosage, and less than about 3–5 mg boron per day. More preferred boron containing structures may provide at least 0.5 mg of boron per serving. Such dosages are expected to be completely safe. Complexes with two mannitol or sorbitol ligands complexed to a single borate center are naturally present in celery, radishes, peaches and other foods. Penn, S. G., et al., "Direct Analysis of Sugar Alcohol Borate Complexes in Plant Extracts by Matrix-Assisted Laser Desorption/Ionization Fourier Transform Mass Spectrometry", Anal. Chem., (1997) 69: 2471–2477; Hu, H. et al., "Isolation and Characterization of soluble boron Complexes in Higher Plants", (1997) 113: 649–655. As used herein, the terms "boron complex", "boron compound/complex", "sugar boron complex", and "boron containing structure" are used interchangeably.

However, and particularly depending on the specific ligands and method of use, higher dosages are also considered suitable for use herein. For example, where the boron containing structure is employed in a method of reducing pain, higher dosages may be appropriate and will typically include dosages between 0.1 and 30 mg per day (and even higher). On the other hand, and,especially where administration of,contemplated compounds is over an extended period (i.e. more than 1 week), lower dosages are also considered suitable.

Experiments

When synthesizing boron compounds/complexes according to the present disclosure, one should generally follow accepted rules of chemical synthesis. Thus, if a ligand contains only one hetero-atom in its B-binding site, one takes four or more molar equivalents of it in respect to one molar equivalent of the starting boron compound. Further, if a ligand contains two or three hetero-atoms in its B-binding sites, one takes two or more molar equivalents of it in respect to one molar equivalent of the starting boron compound. Still further, if a ligand contains four or more hetero-atoms in its B-binding sites, one takes one or more equivalents of the ligand to one molar equivalent of the starting boron compound. Of course, the molar equivalent of the starting boron compound corresponds to its molecular formula if it contains one boron atom in it. If molecular formula contains more than one boron atom one divides molecular formula with a number of boron atoms containing in it. For example, if one starts with sodium tetraborate decahydrate, its molecular formula should be divided by four to obtain its molar equivalent.

General Preparation Procedure of Boron Compounds/Complexes

As a rule, the selected ligand, in the corresponding or slightly higher molar ratio to the starting boron compound and the starting boron compound (most often boric acid or borax), is mixed in water to make a rather concentrated solution (usually in the range from 10 to 30%). The reaction mixture is stirred or shaken at room temperature for 0.5 to 1 hour, whereupon all solid components go completely to a solution. If boric acid is used, then subsequent neutralization is needed, such as with $NaHCO_3$, $KHCO_3$, $CaCO_3$, etc.

Reaching this point, one can proceed further according to one of the two possibilities: using the prepared solution (in undiluted or diluted form) for the final formulation preparation, or if one needs pure and chemically better defined complexes, or using the prepared solution for the isolation and purification of the desired B-complex.

EXAMPLE 1

Calcium Boro-mannitol (Calcium Mannitolo-borate)

Boric acid (1.24 g; 20 mmoles) and mannitol (7.28 g; 40 mmoles) are dissolved in water (20 ml) at 60°–70°C. After cooling down to room temperature, solid calcium carbonate (1 g; 10 mmoles) is gradually added the solution. During the addition of calcium carbonate carbon dioxide is evolved. When all calcium carbonate is dissolved and carbon dioxide evolution ceased (which at lasts about 30 minutes), one adds ethanol (80 ml). Viscous (semi-solid) heavy layer separates out and the upper aqueous-ethanolic solution is decanted off. A new portion of ethanol is added (80 ml), whereupon, on stirring at room temperature for a while, the crystalline complex separated out.

The same is filtered off and washed with ethanol (40 ml). After drying the complex in a vacuum desicator, one obtains pure crystalline Ca-mannito-borate (7 g; 90% of theoretical yield). A similar procedure can be carried out using other cations, such as those of magnesium and potassium, and such may be preferred to avoid phosphates in the skin precipitating the calcium.

EXAMPLE 2

Sodium Serine/Borate Complex (In Aqueous Solution)

Sodium tetraborate (0.804 g; 4 mmoles) and serine (3.2 g; 32 mmoles) are mixed in water (10 ml) at room temperature. After stirring or shaking for 0.5 to 1 hour at room temperature, all components go into solution. The final concentration is adjusted to the desired level (usually 2–4 mg B/ml).

EXAMPLE 3

Calcium Fructoborate Complex

Boric Acid (0.62 g; 10 mmoles) and fructose (3.60 g; 20 mmoles) are mixed in water (10 ml) at room temperature. Solid $CaCO_3$ (1 g; 10 mmoles) is slowly added to the solution in order to control evolution of carbon dioxide. After stirring or shaking for 0.5 to 1 hour at room temperature, all components go into solution. If a solution is the desired finished product form, the final concentration is adjusted to the desired level (usually 2–4 mg B/ml). If a solid Ca fructoborate is desired finished product form, then the final solution is freeze dried to a solid powder with about 2% water content.

EXAMPLE 4

Potassium Boroascorbate

Boric Acid (0.62 g; 10 mmoles) and ascorbic acid (3.56 g; 20 mmoles) are mixed in water (10 ml) at room temperature. Solid $KHCO_3$ is slowly added to the solution in order to control evolution of carbon dioxide. After stirring or shaking for 0.5 to 1 hour at room temperature, all components go into solution. If a solution is a finished product form, the final concentration is adjusted to the desired level (usually 2–4 mg B/ml). If a solid K Boroascorbate is a finished product form, then the final solution is freeze dried to a solid powder with max 2% water content.

EXAMPLE 5

Determination of Enzyme Inhibition

COX-1 enzyme inhibition study was performed using a protocol similar to protocols previously described (see e.g., Riendeau D, et al. in Brit. J. Pharmacol. (1997) 121:105–117; or Warner et al. in Proc. Natl. Acad.Sci. (1999) 96:7563–7568). Typically, the source material was human platelets using endogenous arachidonic acid (Vehicle 1% DMSO) at a preincubation time of 15 min at 37 Centigrades and an incubation time of 15 min at 37 Centigrades (Incubation buffer was HBSS buffer with 15mM HEPES pH7.4). Quantitative analysis was performed via EIA determination of $PGE_2$.

COX-2 enzyme inhibition study was performed using a protocol similar to protocols previously described (see e.g., Riendeau D, et al. in Can. J. Physiol. Pharmacol. (1997) 75:1088–11095; or Warner et al. in Proc. Natl. Acad.Sci. (1999) 96:7563–7568). Typically, the source material was human recombinant Sf9 cells using 0.3 microM arachidonic acid (Vehicle 1% DMSO) at a preincubation time of 15 min at 37 Centigrades and an incubation time of 15 min at 37 Centigrades (Incubation buffer was 100 mM Tris 1 mM Glutathione, 1 microM hematin, and 0.5mM phenol, pH7.7). Quantitative analysis was performed via ETA determination of $PGE_2$.

What is claimed is:

1. A method of inhibiting a prostaglandin endoperoxide synthase enzyme comprising presenting the enzyme with a boron containing structure having a tetrahedral boron atom covalently bound to four ligands at a concentration effective to inhibit the enzyme, and wherein the boron atom is bound to the ligand to form a five- or six- membered ring comprising the boron atom, two hetero-atoms and two or three carbon atoms.

2. The method of claim 1 wherein the enzyme comprises cyclooxygenase-2.

3. The method of claim 1 wherein the enzyme is disposed within a cell.

4. The method of claim 1 wherein at least one of the ligands includes an atom selected from the group consisting of oxygen, nitrogen, carbon, and sulfur, and wherein the boron is covalently bound to the atom.

5. The method of claim 1 wherein the ligand is selected from the group consisting of a saccharide, an amino acid, and an ascorbic acid.

6. The method of claim 1 wherein at least one of the ligands in the boron containing structure imparts an at least 18-fold selectivity of inhibition of cyclooxygenase-2 over cyclooxygenase-1.

7. The method of claim 6 wherein the at least one of the ligands comprises salicylic acid.

8. The method of claim 7 wherein the boron containing structure comprises potassium boroascorbate.

9. The method of claim 1 wherein the boron containing structure forms a complex having an association constant of at least 50.

10. The method of claim 1 wherein the boron containing structure forms a complex having an association constant between about 3,000 to about 20,000.

11. The method of claim 1 wherein the boron containing structure includes a cation selected from the group consisting of sodium, potassium, magnesium and calcium.

12. A method of inducing apoptosis in a cell, comprising presenting the cell with a boron containing structure having a tetrahedral boron atom covalently bound to four ligands at a concentration effective to induce apoptosis, and wherein the boron atom is bound to the ligand to form a five- or six-membered ring comprising the boron atom, two hetero-atoms and two or three carbon atoms.

13. The method of claim 12 wherein the cell is a neoplastic cell.

14. The method of claim 13 wherein the neoplastic cell is a colon cancer cell.

15. The method of claim 12 wherein at least one of the ligands includes an atom selected from the group consisting of oxygen, nitrogen, carbon, and sulfur, and wherein the boron is covalently bound to the atom.

16. The method of claim 15 wherein the ligand is selected from the group consisting of a saccharide, an amino acid, and an ascorbic acid.

17. A method of reducing pain in a patient, comprising administering to patient a boron containing structure having a tetrahedral boron atom covalently bound to four ligands at a dosage effective to reduce pain, wherein the boron atom is bound to the ligand to form a five- or six-membered ring comprising the boron atom, two hetero-atoms and two or three carbon atoms, and wherein at least one of the hetero-atoms is oxygen.

18. The method of claim 17 wherein the pain is not associated with an inflammatory condition.

19. The method of claim 18 wherein the pain is selected from a head ache, a tooth ache and a premenstrual pain.

20. The method of claim 17 wherein at least one of the ligands includes an atom selected from the group consisting of oxygen, nitrogen, carbon, and sulfur, and wherein the boron is covalently bound to the atom.

21. The method of claim 17 wherein the ligand is selected from the group consisting of a saccharide, an amino acid, and an ascorbic acid.

22. A method of reducing inflammation in a patient, comprising administering to the patient a composition comprising a boron containing structure having a tetrahedral boron atom covalently bound to four ligands at a concentration effective to inhibit a prostaglandin endoperoxide synthase, wherein the boron atom is bound to the ligand to form a five- or six-membered ring comprising the boron atom, two hetero-atoms and two or three carbon atoms, and wherein at least one of the hetero-atoms is oxygen.

23. The method of claim 22 wherein the inflammation is associated with arthritis.

* * * * *